US011993758B2

(12) United States Patent
Mohamed

(10) Patent No.: US 11,993,758 B2
(45) Date of Patent: May 28, 2024

(54) TUNABLE PROCESSES FOR THE CONTINUOUS REFINING OF EDIBLE OILS AND FATS

(71) Applicant: CHEMTOR, LP, Lockhart, TX (US)

(72) Inventor: Rana K. Mohamed, Austin, TX (US)

(73) Assignee: Chemtor, LP, Lockhart, TX (US)

( * ) Notice: Subject to any disclaimer, the term of this patent is extended or adjusted under 35 U.S.C. 154(b) by 0 days.

(21) Appl. No.: 17/660,549

(22) Filed: Apr. 25, 2022

(65) Prior Publication Data
US 2023/0340360 A1 Oct. 26, 2023

(51) Int. Cl.
*C11B 3/06* (2006.01)
*C07C 51/41* (2006.01)

(52) U.S. Cl.
CPC .............. *C11B 3/06* (2013.01); *C07C 51/41* (2013.01)

(58) Field of Classification Search
CPC .............. C11B 3/06; C11B 3/16; C07C 51/41
See application file for complete search history.

(56) References Cited

U.S. PATENT DOCUMENTS

| 7,207,445 | B2* | 4/2007 | Manna ............... B01D 11/0449 210/511 |
| 7,618,544 | B2 | 11/2009 | Massingill, Jr. |
| 7,828,978 | B2 | 11/2010 | Geier et al. |
| 7,888,520 | B2 | 2/2011 | Reaney et al. |
| 7,935,734 | B2 | 5/2011 | Tonkovich et al. |
| 9,468,866 | B2* | 10/2016 | Massingill ............... C07C 29/76 |
| 9,815,001 | B2* | 11/2017 | Massingill ............... C07D 333/76 |
| 9,833,009 | B2 | 12/2017 | Anijs et al. |
| 9,969,952 | B2 | 5/2018 | Norn et al. |
| 11,198,107 | B2 | 12/2021 | Davis et al. |
| 2006/0157411 | A1* | 7/2006 | Massingill ......... B01D 11/0449 210/639 |
| 2006/0189815 | A1 | 8/2006 | Tou |
| 2007/0214712 | A1* | 9/2007 | Garwood ............. B01J 19/0093 44/308 |
| 2013/0030205 | A1 | 1/2013 | Jackson et al. |
| 2021/0069667 | A1* | 3/2021 | Davis .................. B01J 19/2415 |

FOREIGN PATENT DOCUMENTS

| CN | 106720821 B | 5/2020 |
| EP | 2 508 078 A1 | 10/2012 |
| EP | 2 508 079 A1 | 10/2012 |
| EP | 2 352 382 B1 | 5/2014 |
| JP | 6905649 B1 | 7/2021 |
| VN | 28222 A | 12/2011 |
| VN | 10023625 B | 5/2020 |
| WO | WO 2009/017909 A2 | 2/2009 |

OTHER PUBLICATIONS

International Search Report and Written Opinion issued by the United States Patent and Trademark Office as International Searching Authority for International Application No. PCT/US2023/019744, dated Sep. 21, 2023, 23 pgs.

* cited by examiner

Primary Examiner — Yate' K Cutliff
(74) Attorney, Agent, or Firm — Haynes and Boone, LLP

(57) ABSTRACT

A system for purifying edible oils includes a plurality of microchannel fiber reactors arranged in series. The edible oils may be first neutralized with an alkali solution and then washed with water to thereby remove impurities such as free fatty acids, mono- and diacylglycerols, phospholipids, glycolipids, trace metals, and unsaponifiable matter. The system allows for continuous, high-yield production of improved quality edible oils.

13 Claims, 8 Drawing Sheets

*Mode 1: Kinetic Purification Cascade*

*Mode 2: Thermodynamic Fractionation*

TUNABLE PROCESSES FOR THE CONTINUOUS REFINING OF EDIBLE OILS AND FATS

TECHNICAL FIELD OF THE DISCLOSURE

The present disclosure generally relates to the design and operational modes of a high throughput microchannel reactor for industrial scale chemical refining in continuous flow. More specifically, the disclosure relates the application of this system to the chemical refining of edible oils and fats (e.g., crude cocoa butter).

BACKGROUND

Chemical and physical processes for the refining of edible oils and fats emerged to address challenges in the poor quality and shelf life of oils that were produced through solvent extractions. Such processes typically include a combination of degumming, neutralization, and dewaxing steps which often terminate in a final bleaching or deodorization step to ensure optimal taste, aroma, appearance, and stability of the edible oil product. The optimal process flow depends on several factors such as the type of oil, the corresponding impurity profile, and the markets the final oil product aims to supply.

In the confectionary industry, Theobroma oil (i.e., cocoa butter) is an essential ingredient which contributes to the gloss, texture, and crystallization behavior of chocolate. Crude cocoa butter is predominantly composed of triacylglycerides (also referred to herein as triacylglycerols or TAGs) (≥95 wt %) but typically has a sour flavor and odor due to minor contaminants such as free fatty acids (FFAs), mono- and diacylglycerols (DAGs), phospholipids, glycolipids, trace metals and unsaponifiable matter. To comply with the EU directive 2000/36/EC (2000), which limits the final respective FFAs and unsaponifiable matter concentrations to ≤1.75 wt % and ≤0.5 wt %, crude cocoa butter must undergo refining. Although steam refining is typically successful in removing most quality-compromising contaminants, the process is highly energy intensive-requiring temperatures of ≥200° C.—and results in poor crystallization behavior and a bland taste in the final purified butter. Consequently, a mild and cost-effective chemical refining process for the removal of FFAs and other undesirable contaminants is necessary to obtain good quality cocoa butter amenable to a mild sequential (i.e., lower temperature 160° C.) steam stripping deodorization step that preserves the residual aroma desired in the final product.

The need for a chemical solution is pressing considering recent trends indicating a steady annual increase of the volume of cocoa butter with >1.75 wt % concentration of FFAs due to improper handling of cocoa beans, unpredictable crop history, and wet post-harvest conditions. At higher concentrations, free fatty acids negatively impact the butter's crystallization behavior and decrease its stability against oxidation. The effect of other organic contaminants, such as phospholipids, on the crystallization behavior of cocoa butter is more complex and has been reported to be species dependent. Generally, phospholipid concentrations comprise a range of 0.26-0.94 wt % of cocoa butter mass. The structural characterization of these compounds has identified a wide compositional array including diphosphatidylglycerol (DPG), phosphatidylglycerol (PG), phosphatidylethanolamine (PE), phosphatidylcholine (PC), phosphatidylinositol (PI), lysophosphatidylethanolamine (LPE), lysophosphatidylcholine (LPC) and phosphatidic acid (PA).

Due to the different packing configurations the triglycerides (predominantly POP, SOS, and POS) in cocoa butter can adopt, cocoa butter is a polymorphous fat which has unique physical properties such as multiple-melting points and variable crystallization kinetics. As a result, the bulk phase behavior of cocoa butter in standard chemical refining processes using aqueous solutions can be quite unpredictable and particularly sensitive to batch dependent fluctuations in contaminants. For example, in the FFA neutralization process using aqueous alkali, phospholipids present can behave as aggressive surfactants and form lipophilic mixed aggregates with the generated FFA salts. Although the concentration of phospholipids in crude cocoa butter is low relative to other edible oils, their presence presents a significant challenge during chemical extractions due to their low Critical Micelle Concentration (CMC). At the critical phospholipid concentration, typically in the micromolar and nanomolar range for C18 and C16 lipid chains, the amphiphilic phospholipids self-assemble into aggregates with variable morphologies, in turn complicating the separation of the aqueous effluent from the purified triglycerides. This results in inefficient low-yielding extractions due to the formation of kinetically stable emulsions further exasperated by stabilization mechanisms characteristic of cocoa butter's triglyceride profile.

BRIEF DESCRIPTION OF THE DRAWINGS

Various embodiments of the present disclosure will be understood more fully from the detailed description given below and from the accompanying drawings. In the drawings, like reference numbers may indicate identical or functionally similar elements. Embodiments are described in detail hereinafter with reference to the accompanying figures, in which.

DETAILED DESCRIPTION

Figure 1:
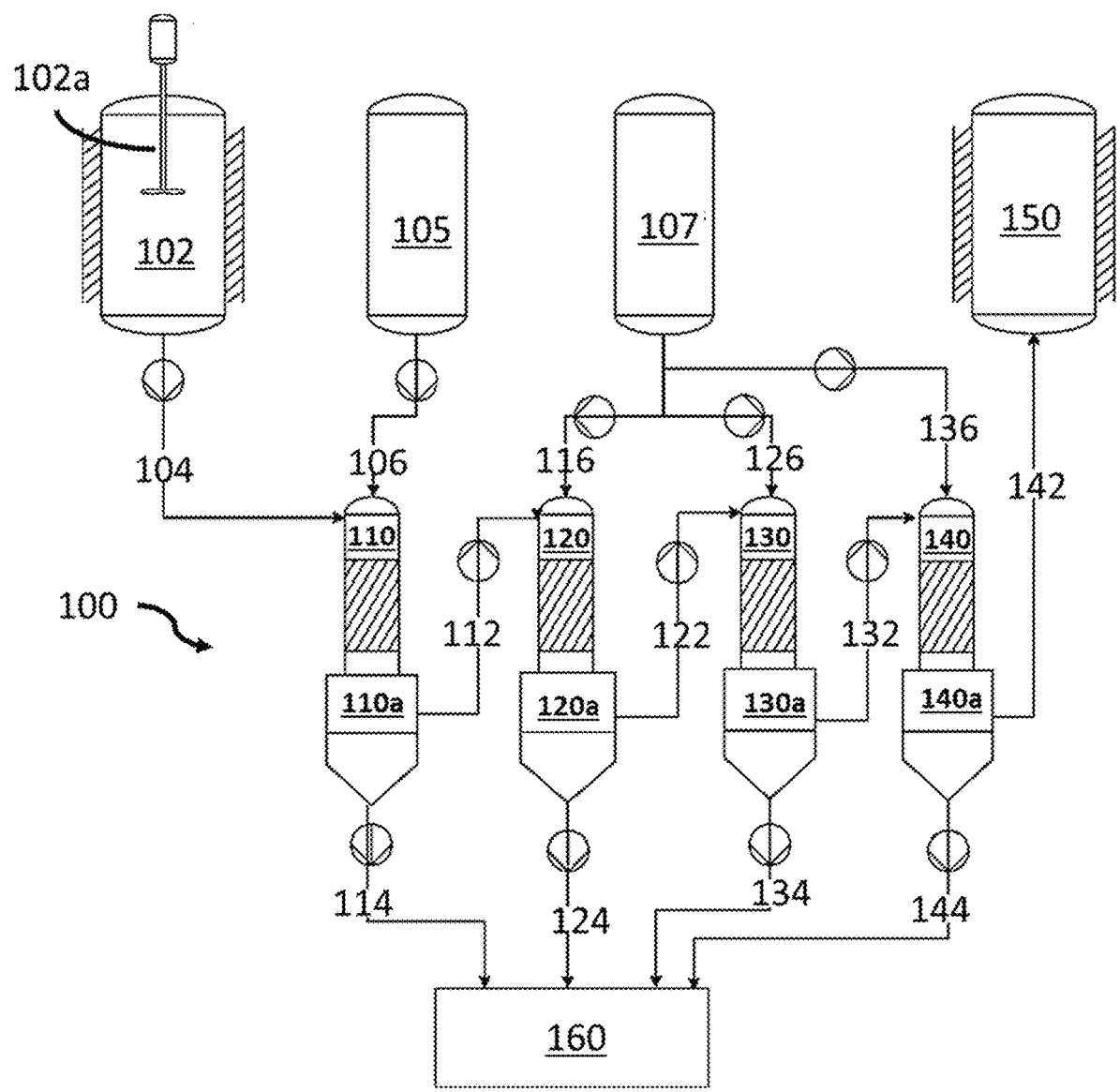
FIG. 1 is a schematic diagram showing an edible oil purification system according to an embodiment of the present disclosure.

The following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure relates to the chemical refining of edible oils and fats (e.g., crude cocoa butter). Depending on the tunable mode of operation, the critical micelle concentrations (CMC) of surfactants produced in the acid-base extractions can be modified to impact the spatial distribution of mass in the refined product and effluent streams, in turn increasing conversion, yield and overall quality of product. Various modes of the microchannel reactor operations may be used, targeting either one or multiple distinct fractionated product streams. This methodology enables the conversion of crude mixtures of triglycerides into higher quality oils and fats amenable to the milder sequential refining steps necessary to meets market requirements at minimal cost.

The aggregate morphologies and phase separation of natural cocoa butter and aqueous alkali mixtures are highly dependent on factors such as temperature, pH, concentration, salinity, and flow conditions. The intractable formation of stabilized cocoa butter emulsions during chemical refining is exasperated via the Pickering stabilization mechanism and results in unpredictable morphologies and spontaneous aggregation due to minor changes in pH and different caustic concentrations.

According to embodiments of the present disclosure, a plurality of microchannel fiber reactors may be used to optimize high aspect ratio reaction channels in which diffusion rates and mass transfer between oleaginous and aqueous solutions are accelerated. The microchannel fiber reactor may be fabricated via the uniform vertical suspension of micron-sized stainless-steel fiber enclosed in a cylindrical reactor shell (see, e.g., U.S. Pat. Nos. 7,618,544 and 11,198,107, each of which is hereby incorporated by reference in its entirety).

Referring to FIG. 1, a system 100 for refining an edible fat or oil ("edible oil") includes an oil supply 102 containing the edible oil to be processed. The edible oil may include a mixture of triglycerides, FFA, phospholipids, and other minor contaminants. In some embodiments, the edible oil may include about 0.5 to about 8 wt %, about 1 to about 5 wt %, or about 2 to about 4 wt % of FFA.

In some embodiments, the oil supply 102 may include an agitation mechanism 102a, such as a stirrer. In some embodiments, the oil supply 102 may be maintained at or above a melting point of the edible oil (e.g., at least 60° C., at least 70° C., or at least 80° C.). In some embodiments, the entire system 100 may be maintained at or above a melting point of the edible oil. The edible oil is transported from the oil supply 102 via line 104 to a first reactor 110, which may be a microchannel fiber reactor.

An aqueous reactant solution or extraction solution ("reactant solution") is simultaneously supplied to the first reactor 110 via line 106 from a reactant supply 105. The reactant solution may include an aqueous reactant such as a solution including NaOH, KOH, and the like and/or may include an extractant, such as water. In some embodiments, the amount of base in the reactant solution is from 0.2 to 2.0, from 0.5 to 1.2, about 0.5, about 1.0, or about 1.2 molar equivalents, based on the amount of FFA in the edible oil. The edible oil reacts with reactant solution in the first reactor 110—which controllably contact the reactants with minimal perturbations in concentration, temperature, and flow under continuous operations—to form reaction products. The structured vertical suspension and packing of the fibers within the reactor serve the function of providing an inert scaffold comprising thousands of microfluidic channels in which the acid-base reaction occurs with high efficiency, enabling very precise dosing of reactant (e.g., NaOH) and rapid formation of products (e.g., lipid salts). Inside the microchannels, the FFAs of the edible oil undergo a rapid acid base reaction with the NaOH in which free fatty acid sodium salts and water are formed and migrate into the aqueous phase.

The reaction products are collected in a first separator 110a of the first reactor 110, wherein the reaction products include a first raffinate including the edible oil having a first impurity removed therefrom and a first aqueous waste stream including the reactant solution and the first impurity. The first impurity may include, e.g., FFA and may be a combination of impurities. The aqueous reactant solution (in some embodiments having a high pH) readily separates from the oleaginous triglycerides of the edible oil (e.g., cocoa butter) by natural phase separation after exiting the microchannel reactor wherein the higher density aqueous phase concentrates in the bottom of a first separator 110a. The first aqueous waste stream is removed from the first separator 110a via line 114 into an aqueous effluent tank 160, which may include a recycling system to separate the water, the first impurity, and/or the reactant for further use. The lower density neutralized edible oil raffinate (first raffinate) may be continuously collected from the top of the first separator 110a and directed via line 112 to a second reactor 120, which may be a microchannel fiber reaction.

An aqueous solution, such as water, is simultaneously supplied from aqueous tank 107 via line 116 to the second reactor 120. The aqueous solution thereby washes the first raffinate in the second reactor 120 and the resulting first wash products are collected in a second separator 120a. The first wash products include a second raffinate including the first raffinate having a second impurity removed therefrom (which may be of the same kind or different from the first impurity) and a second aqueous waste stream including the aqueous solution and the second impurity. The second aqueous waste stream is removed from the second separator 120a via line 124 to the aqueous effluent tank 160. The second raffinate is directed via line 122 to a third reactor 130, which may be a microchannel fiber reactor.

An aqueous solution is simultaneously supplied from the aqueous tank 107 via line 126 to the third reactor 130. The aqueous solution thereby washes the second raffinate in the third reactor 130 and the resulting second wash products are collected in a third separator 130a. The second wash products include a third raffinate including the second raffinate having a third impurity removed therefrom (which may be of the same kind or different from the first and/or second impurity) and a third aqueous waste stream including the aqueous solution and the third impurity. The third aqueous waste stream is removed from the third separator 130a via line 134 to the aqueous effluent tank 160. The third raffinate is directed via line 132 to a fourth reactor 140, which may be a microchannel fiber reactor.

An aqueous solution is simultaneously supplied from the aqueous tank 107 via line 136 to the fourth reactor 140. The aqueous solution thereby washes the third raffinate in the fourth reactor 140 and the resulting third wash products are collected in a fourth separator 140a. The third wash products include a fourth raffinate including the third raffinate having a fourth impurity removed therefrom (which may be of the same kind or different from the first, second, and/or third impurity) and a fourth aqueous waste stream including the aqueous solution and the fourth impurity. The fourth aqueous waste stream is removed from the fourth separator 140a via line 144 to the aqueous effluent tank 160. The fourth raffinate is directed via line 142 to pure edible oil tank 150.

Although the system 100 described above includes four reactors, any number of reactors may be used. In some embodiments, any of the reactors may differ from one or more of the other reactors in terms of temperature, types of fibers, length, diameter, and/or packing density. See U.S. Pat. No. 11,198,107.

In the system 100, the facile and essentially instantaneous separation of raffinate from effluent results in a high recovery of the refined CB (>99%). In some embodiments, the system 100 can yield a purified cocoa butter with minimal losses of TAGs and DAGs. In some embodiments, the system 100 results in a preferential extraction of DAGs over TAGs or vice versa.

Figure 2:
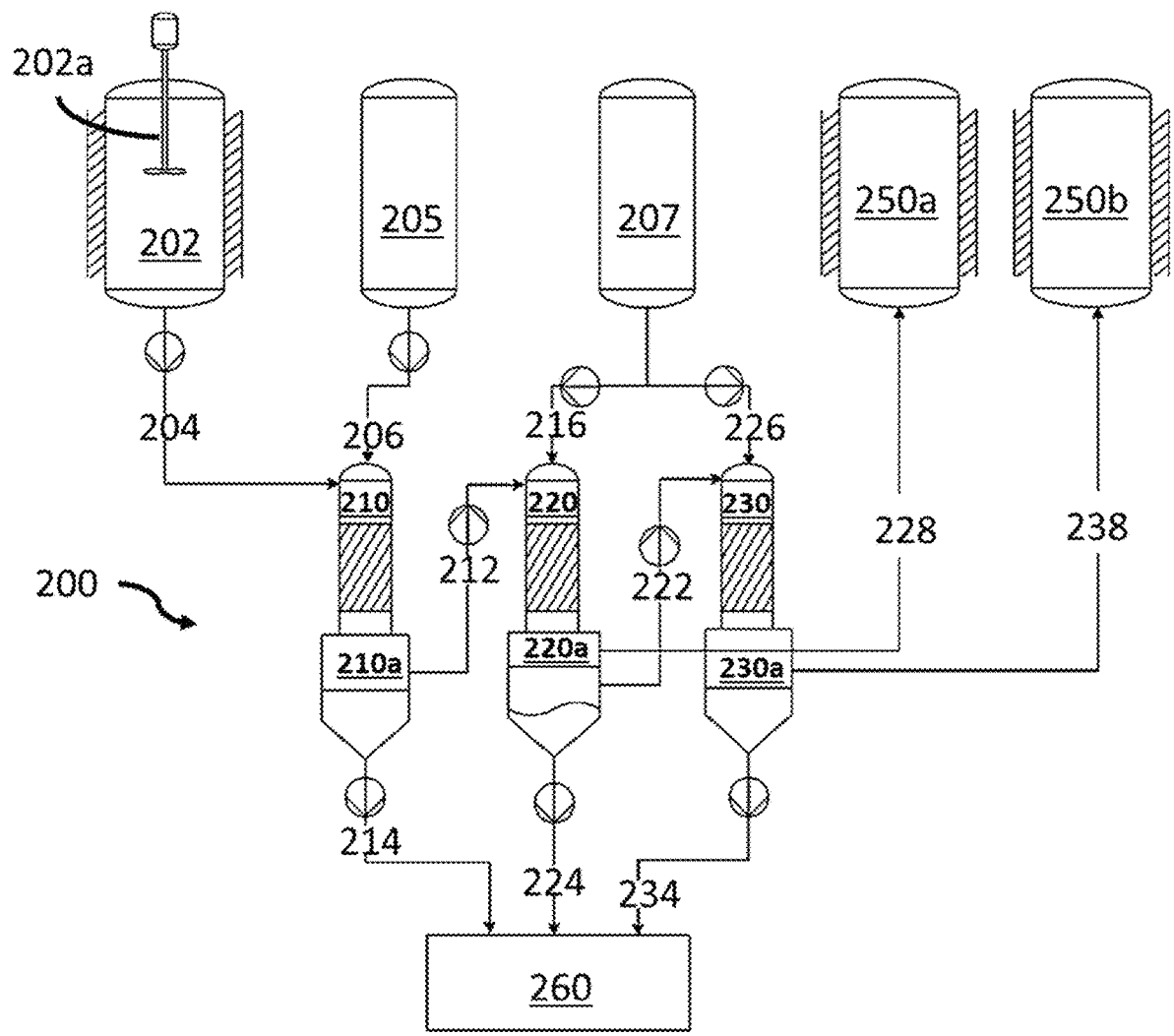
FIG. 2 is a schematic diagram showing an edible oil purification system according to another embodiment of the present disclosure

Turning to FIG. 2, a system 200 for refining an edible oil is shown. Unless indicated otherwise, components of the system 200 may be the same as those described for system 100 above. The system 200 includes an oil supply 202 containing the edible oil to be processed. In some embodiments, the oil supply 202 may include an agitation mechanism 202a, such as a stirrer. In some embodiments, the oil supply 202 may be maintained at or above a melting point of the edible oil (e.g., at least 60° C., at least 70° C., or at least 80° C. In some embodiments, the entire system 200 may be maintained at or above a melting point of the edible oil. The edible oil is transported from the oil supply 202 via line 204 to a first reactor 210, which may be a microchannel fiber reactor.

An aqueous reactant solution is simultaneously supplied to the first reactor 210 via line 206 from a reactant supply 205. The reactant solution may be as described above. The edible oil reacts with reactant solution in the first reactor 210 to produce reaction products. The reaction products are collected in a first separator 210a of the first reactor, wherein the reaction products include a first raffinate including the edible oil having a first impurity removed therefrom and a first aqueous waste stream including the reactant solution and the first impurity. The first impurity may include, e.g., FFA and may be a combination of impurities. The first aqueous waste stream is removed from the first separator 210a via line 214 into an aqueous effluent tank 260, which may include a recycling system to separate the water, the first impurity, and/or the reactant for further use. The first raffinate is directed via line 212 to a second reactor 220, which may be a microchannel fiber reaction.

An aqueous solution, such as water, is simultaneously supplied from aqueous tank 207 via line 216 to the second reactor 220. The aqueous solution thereby washes the first raffinate in the second reactor 220 and the resulting first wash products are collected in a second separator 220a. The first wash products include a first purified edible oil (a top layer) which may be removed from the second separator via line 228 to a first pure edible oil tank 250a. The first wash products further include a second raffinate (a middle layer) including the first raffinate having a second impurity removed therefrom (which may be of the same kind or different from the first impurity) and a second aqueous waste stream (bottom layer) including the aqueous solution and the second impurity. The second aqueous waste stream is removed from the second separator 220a via line 224 to the aqueous effluent tank 260. The second raffinate is directed via line 222 to a third reactor 230, which may be a microchannel fiber reactor.

An aqueous solution is simultaneously supplied from the aqueous tank 207 via line 226 to the third reactor 230. The aqueous solution thereby washes the second raffinate in the third reactor 230 and the resulting second wash products are collected in a third separator 230a. The second wash products include a second purified edible oil including the second raffinate having a third impurity removed therefrom (which may be of the same kind or different from the first and/or second impurity) and a third aqueous waste stream including the aqueous solution and the third impurity. The third aqueous waste stream is removed from the third separator 230a via line 234 to the aqueous effluent tank 260. The second purified edible oil is directed via line 238 to a second pure edible oil tank 250b, wherein the second purified edible oil comprises a distinct composition from the first purified edible oil.

Although the system 200 described above includes four reactors, any number of reactors may be used. In some embodiments, any of the reactors may differ from one or more of the other reactors in terms of temperature, types of fibers, length, diameter, and/or packing density. See U.S. Pat. No. 11,198,107.

Figure 3:
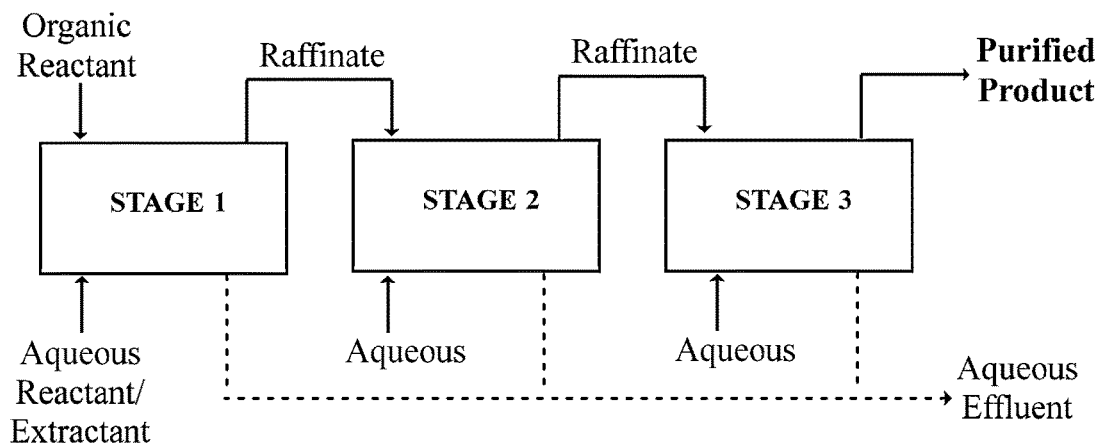
FIG. 3 is a schematic diagram showing two modes of continuous operations of a microchannel fiber reactor according to embodiments of the present disclosure.
Figure 3:
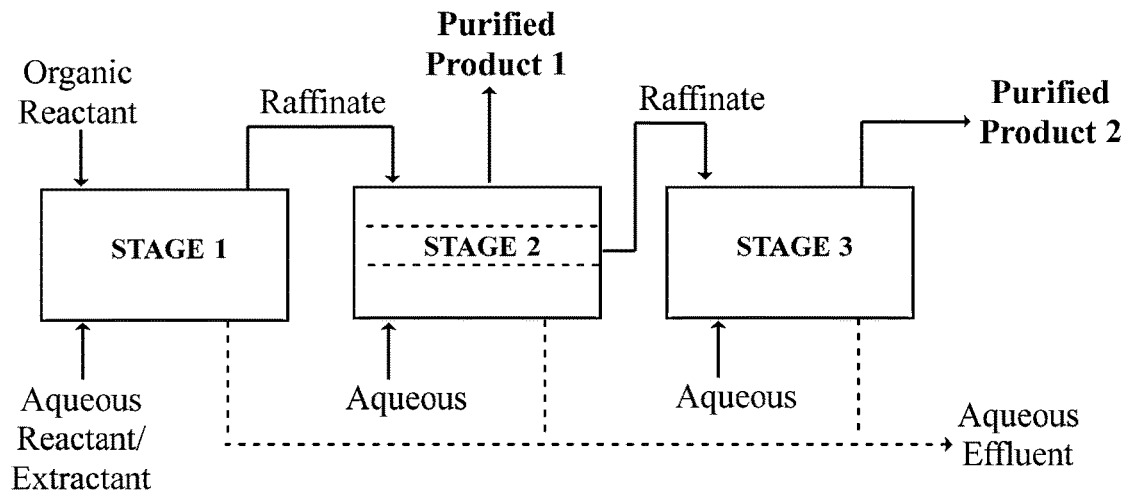

FIG. 3 depicts a simplified overview of the systems 100 and 200. In the kinetic purification cascade (corresponding to system 100), the conditions within the reactors are tuned to maintain two phases in each separator. As compared with the thermodynamic fractionation (corresponding to system 200), the kinetic purification cascade uses shorted residency times (i.e., contact time between reactants) within the reactors to incrementally remove impurities in each subsequent stage. In the thermodynamic fractionation system, the residency times are increased such that three phases are formed in at least on of the reactors, wherein a top layer thereof comprises pure edible oil and the middle layer may undergo further refining. The thermodynamic fractionation system thereby produces two distinct purified products.

In both modes of operation, the first reactor in the multistage microchannel reactor series is used to first contact the two immiscible phases—the crude triglyceride mixture (the edible oil) and the aqueous (basic) solution. The microchannels allow the stable maintenance of the desired operating temperature range and enable the continuous formation of fresh interfaces between the immiscible fluids as a function of the enhanced surface area inherent in the plurality of the fiber packing material. The generated surfactants subsequently adsorb onto the freshly created interfaces which are continuously generated and controlled via the shear rate which can be modified by controlling the injection flowrate of the solutions and the reactor pack density. The gradient in surfactant concentration affects the flow around the interfaces and enables the separation of surfactants from the edible oil phase into the aqueous effluent. The net result is a facile, simultaneous neutralization of the injected edible oil and separation from the aqueous effluent phase.

The tunable process disclosed herein incorporates the staging of fiber reactors in series that continuously remove FFAs, phospholipids, and metals from natural, unrefined cocoa butter. As described above, each reactor stage can be optimized to target select impurities and sequentially reduce the total contaminants present in the feed oil, in some embodiments using solely alkali and water. The reactor packing enables simultaneous contact and separation of the product streams from the effluent waste streams. At each stage, the spent wash water readily separates from the purified cocoa butter, eliminating the need for extensive settling time. The net result is the high-yield, continuous production of purified edible oils and, in the case of cocoa butter, purified cocoa butter with low FFA, low moisture content, and improved color and crystallization behavior (BCI). Integration of the fiber reactor assembly into cocoa processing facilities offers the opportunity for great improvements to upstream and downstream processing units.

In some embodiments, the purified oil (i.e., the second, third, or fourth raffinate in system 100 and/or the first or second purified edible oil in system 200) has a significantly reduced content of the targeted impurities, such as FFA, as compared with the starting edible oil. In some embodiments, a weight ratio of FFA in the purified oil to FFA in the edible oil is less than 0.3, less than 0.25, less than 0.2, less than 0.15, less than 0.1, or less than 0.05. In some embodiments, at least 65 wt, at least 70 wt %, at least 75 wt %, at least 80 wt %, at least 85 wt %, at least 90 wt %, at least 95 wt %, or at least 98 wt % of the FFA is removed from the edible oil using the system 100 or 200. In some embodiments, the system 100 or 200 may be configured to remove selected impurities while maintaining other components in the purified oil. For example, in some embodiments, FFA may be removed at the rates mentioned above while maintaining at least 70 wt %, at least 80 wt %, at least 90 wt %, or at least 95 wt % of DAGs and/or TAGs as compared to the starting edible oil. In some embodiments, the system 100 or 200 may be configured to remove FFA and a second impurity while maintaining a third impurity in the purified oil. For example, in some embodiments, FFA may be removed at the rates mentioned above and DAGs may be removed at a rate of at least 30 wt %, at least 40 wt %, at least 50 wt %, or at least 60 wt % as compared to the starting edible oil while maintaining TAGs in the purified oil at a rate of at least 70 wt %, at least 80 wt %, at least 90 wt %, or about 100 wt % as compared to the starting edible oil. In some embodiments, the system 100 or 200 may be configured to remove phospholipids as an impurity from the edible oil. In such embodiments, the phospholipids may be removed at a rate of at least 70 wt %, at least 80 wt %, at least 90 wt %, or about 100 wt % as compared to the starting edible oil.

EXAMPLES

Comparative Example 1

Figure 4:
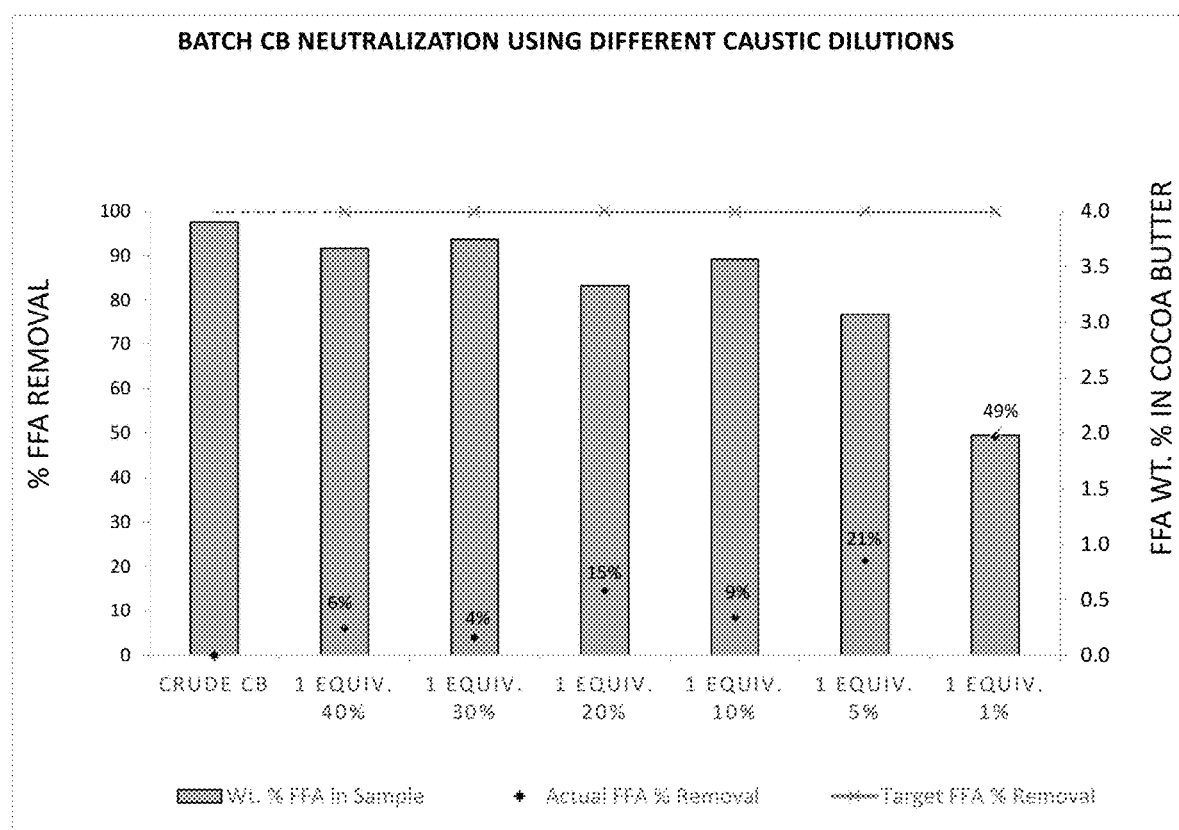
FIG. 4 is a graph showing the results of Comparative Example 1, wherein batch neutralization of crude cocoa butter was conducted using variable caustic dilutions using 1.0 molar equivalents of NaOH relative to the starting FFA.

Batch neutralization of crude cocoa butter was screened using variable caustic dilutions. In a stirred reaction vessel, 100 grams of crude cocoa butter, comprising 3.9 wt % FFA, was heated to 80° C. and separately treated with 1 molar equivalent (relative to starting FFA concentration) of aqueous sodium hydroxide as 40 wt %, 30 wt %, 20 wt %, 10 wt %, 5 wt %, and 1 wt % solutions, respectively. The results are shown in the graph of FIG. 4. All trials resulted in inefficient neutralization (6-49% removal) and poor separation of the cocoa butter triglycerides from the aqueous solution. Higher dilution of the aqueous base marginally improved the reaction efficiency and phase separation but still necessitated long settling time and resulted in significant retention of the generated soaps in the bulk cocoa butter phase. Thus, a high-throughput, low-shear system in which rapid mass transfer is facilitated under tight process controls is critical for the efficient refining of high-value edible oils susceptible to indissoluble aggregate formation and substantial yield losses.

Example 1

Figure 5:
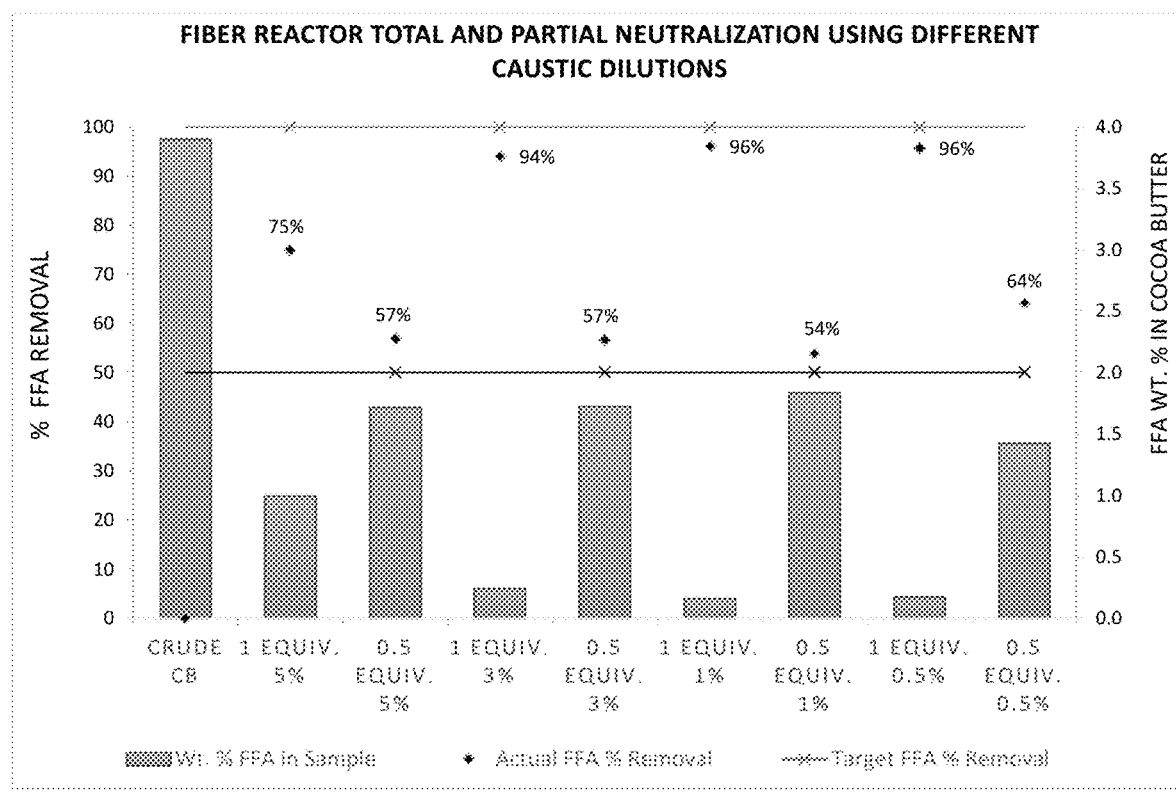
FIG. 5 is a graph showing the results of Example 1.

Crude cocoa butter, comprising of 3.9 wt % FFA (1 molar equiv.), was heated to 80° C. and continuously pumped into the reactor through one injection inlet. In a second injection inlet, an aqueous sodium hydroxide solution was also simultaneously injected, and the flowrate modulated to deliver either 1.0 or 0.5 molar equivalent (relative to the starting FFA concentration) of NaOH at different dilutions. The reactant solutions were allowed to pass through the microchannel reactor and collected from a separator vessel adjoined at the bottom to analyze the reaction efficiency as determined by the percentage of FFA removed from the cocoa butter and the coalescence rate of the two phases. The results are summarized in FIG. 5.

In one microchannel reactor trial, crude cocoa butter comprising 3.9 wt % FFA was injected simultaneously with 1 molar equivalent of NaOH as a 5 wt % aqueous solution at 80° C. and resulted in the removal of 75% of FFA. This corresponds to 3.6× improvement in FFA removal relative to the same conditions in a batch stirred system which only removed 21%.

In a second microchannel reactor trial, targeting the partial reduction of starting FFA concentration by 50%, crude cocoa butter comprising 3.9 wt % FFA was injected simultaneously with 0.5 molar equivalent of NaOH as a 5 wt % aqueous solution at 80° C. and resulted in the removal of 57% of starting FFA, indicating a high degree of controlled reactant dosing and contact within the reactor microchannels.

In a third microchannel reactor trial, crude cocoa butter comprising 3.9 wt % FFA was injected simultaneously with 1 molar equivalent of NaOH as a 3 wt % aqueous solution at 80° C. and resulted in the removal of 94% of FFA.

In a fourth microchannel reactor trial, targeting the partial reduction of starting FFA concentration by 50%, crude cocoa butter comprising 3.9 wt % FFA was injected simultaneously with 0.5 molar equivalent of NaOH as a 3 wt % aqueous solution at 80° C. and resulted in the removal of 57% of starting FFA, indicating a high degree of controlled reactant dosing and contact within the reactor microchannels.

In a fifth microchannel reactor trial, crude cocoa butter comprising 3.9 wt % FFA was injected simultaneously with 1 molar equivalent of NaOH as a 1 wt % aqueous solution at 80° C. and resulted in the removal of 96% of FFA which is a 2× improvement in reaction efficiency relative to batch treatment in a stirred reaction vessel.

In a sixth microchannel reactor trial, targeting the partial reduction of starting FFA concentration by 50%, crude cocoa butter comprising 3.9 wt % FFA was injected simultaneously with 0.5 molar equivalent of NaOH as a 1 wt % aqueous solution at 80° C. and resulted in the removal of 54% of starting FFA, indicating a high degree of controlled reactant dosing and contact within the reactor microchannels.

In a seventh microchannel reactor trial, crude cocoa butter comprising 3.9 wt % FFA was injected simultaneously with 1 molar equivalent of NaOH as a 0.5 wt % aqueous solution at 80° C. and resulted in the removal of 96% of FFA.

In an eighth microchannel reactor trial, targeting the partial reduction of starting FFA concentration by 50%, crude cocoa butter comprising 3.9 wt % FFA was injected simultaneously with 0.5 molar equivalent of NaOH as a 0.5 wt % aqueous solution at 80° C. and resulted in the removal of 64% of starting FFA, indicating a high degree of controlled reactant dosing and contact within the reactor microchannels.

Example 2

Figure 6:
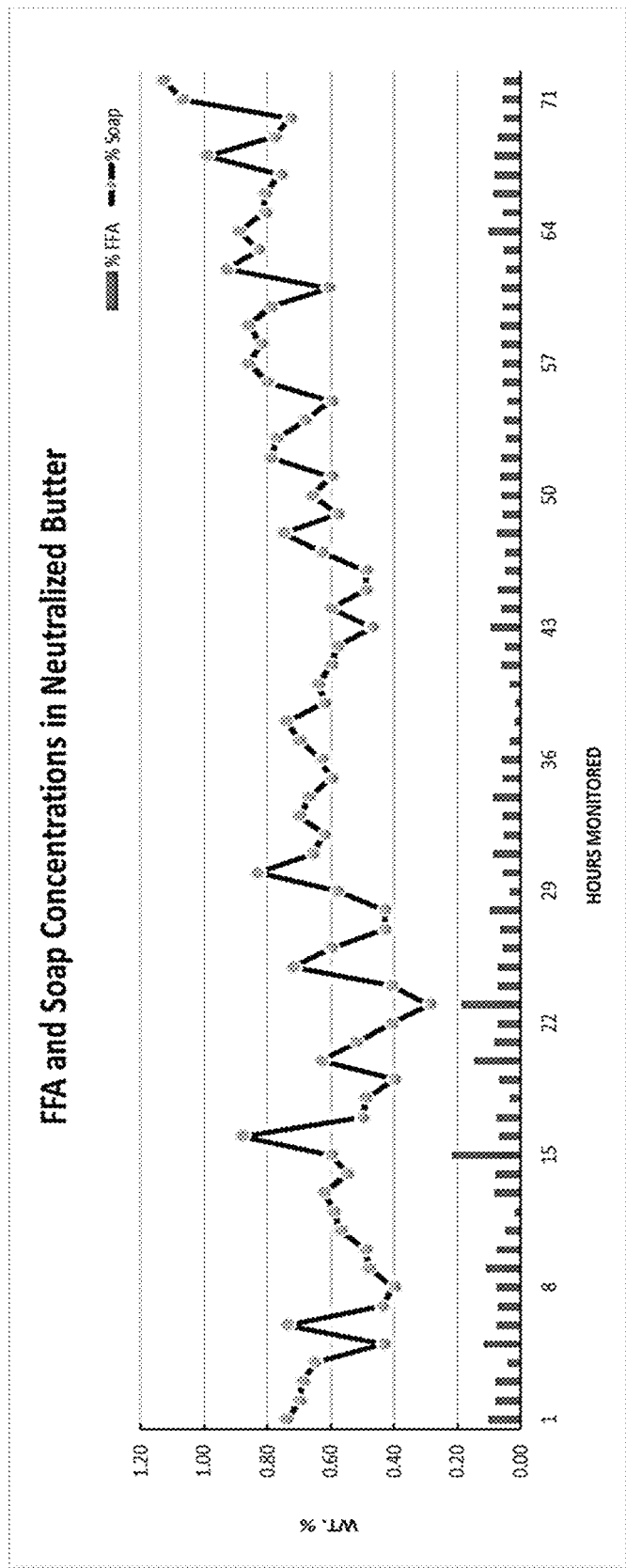
FIG. 6 is a graph showing the stability of neutralized cocoa butter in Example 5.

Crude natural cocoa butter with an initial FFA concentration of 1.91 wt % FFA was neutralized with 0.3 wt % NaOH aqueous solution via simultaneous injection of the two fluids in a microchannel reactor at a 1:1.1 volumetric flowrate ratio of crude cocoa butter to aqueous base. The neutralized butter produced in the first reactor at a production rate of 318 mL/min was continuously monitored every hour for a total of 72 hours and showed a standard deviation of 0.03 and 0.16 wt % in FFA and soap concentrations which averaged to 0.07 wt % and 0.65 wt %, respectively. The results are shown in FIG. 6. Due to the retention of 35% of the generated FFA sodium salts in the cocoa butter layer, a subsequent water wash is necessary for optimal separation.

Example 3

Crude natural cocoa butter with an initial FFA concentration of 2.73 wt % FFA was neutralized with 0.43 wt % NaOH aqueous solution via simultaneous injection of the two fluids into a microchannel reactor in a 1:1 volumetric flowrate ratio of crude cocoa butter to aqueous base at 150 mL/min. The neutralized butter was continuously monitored every hour for a total of 23 hours resulting in 98% removal of FFA, yielding a final concentration of 0.2 wt % in the purified stream. This example demonstrates the ability to efficient remove even high levels of FFA from crude natural cocoa butter according to the method and systems described herein.

Example 4

The neutralized cocoa butter generated by treating crude natural cocoa butter with aqueous caustic in the first microchannel reactor trial of Example 1 was collected and determined by titration to contain 0.65 wt % soap. The phospholipids, L-α-Lysophosphatidylcholine and L-α-phosphatidylinositol, were also identified as present in the neutralized butter. This butter was subsequently injected (at 366 mL/min) into a second microchannel reactor in which solely water was simultaneously injected at 80° C. at a volumetric flow ratio of 1:3 CB:$H_2O$.

Figure 7:
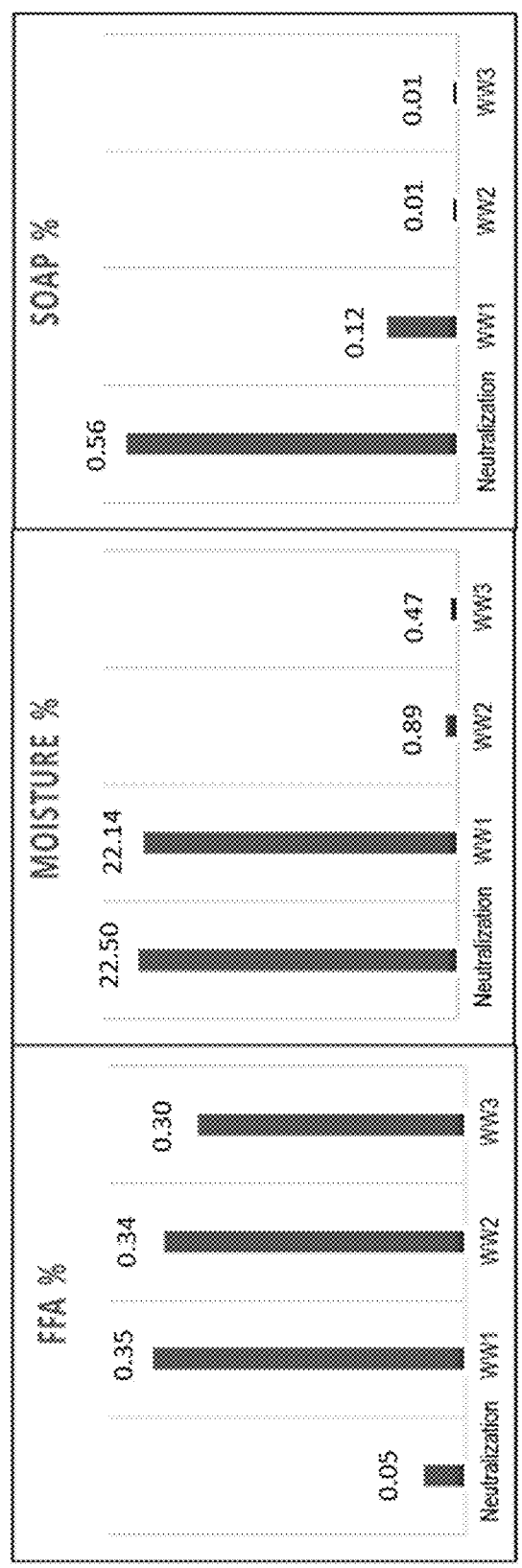
FIG. 7 is a graph showing the sequential changes of the products of Example 5.

This resulted in the separation of three phases in the separator adjoined to the microchannel reactor in which the top and lightest organic stream (product stream 1) comprised of a purified triglyceride mixture in which the initial FFA concentration of the crude cocoa butter was reduced by >90% and 99.5% of the generated soaps were completely removed. Furthermore, product stream 1 continuously phased out as a clarified purified cocoa butter stream with low residual moisture content (0.53 wt % $H_2O$) and distinct chemical composition comprising of 90.88 wt % triglycerides, 3.76 wt % diglycerides, 0.20 wt % FFA, ≤0.01 wt % soap, and selectively enriched only with L-α-Lysophosphatidylcholine (FIG. 7).

The second, slightly heavier organic phase (product stream 2), also comprised predominantly of triglycerides, was titrated every hour for 58 continuous hours to determine an average FFA concentration of 0.18 wt % and soap concentration of 0.18 wt % and was preferentially enriched solely with L-α-phosphatidylinositol. To further purify product stream 2 by reducing the concentration of residual ionic soaps and entrained water, this phase was separately pumped out of the separator adjoined to reactor two and subsequently injected into a third microchannel reactor (at 190 mL/min) in which water was also injected at 80° C. at a volumetric flow ratio of 1:3 organic to water.

The third reactor maximizes the yield of the total triglycerides recovered in this refining process (>99%) and enables the continuous fractionation of a second distinct low moisture product stream. The fully purified product stream 2 was continuously collected out of the top of the separator adjoined to the third reactor for 58 hours and titrated every hour to determine an average FFA concentration of 0.24 wt %, 0.38 wt % water, 0.01 wt % soap. HPLC analysis indicated that product stream 2 is predominantly comprised of 87.04% triglycerides, 3.7 wt % diglycerides and 8.49% wt % L-α-phosphatidylinositol. The results are shown in Table 1 below

TABLE 1

| Measurement method | Measured Property | Product Stream 1 | Product Stream 2 |
|---|---|---|---|
| AOCS Ca 17-01 (ICP-OES) | Total Phosphorous (ppm) | 0.00 | 0.00 |
| AOCS Ca 6a-40 | Unsaponifiable matter (wt %) | 0.55 | 0.55 |
| AOCS Ca 17-01 (ICP-OES) | Iron (ppm) | 0.00 | 0.00 |
| HPLC | Total Diacylglycerol (wt %) | 3.76 | 3.70 |
| HPLC | Total Triacylglycerol (wt %) | 90.88 | 87.04 |
| Titration | FFA (wt %) | 0.20 | 0.24 |
| AOCS Ja 7b-91 | L-α-phosphatidylethanolamine (wt %) | 0.00 | 0.00 |
| AOCS Ja 7b-91 | L-α-phosphatidylinositol (wt %) | 0.00 | 8.49 |
| AOCS Ja 7b-91 | Phosphatidylcholine (wt %) | 0.00 | 0.00 |
| AOCS Ja 7b-91 | L-α-lysophosphatidylcholine (wt %) | 4.62 | 0.00 |

As shown above, thermodynamic fractionation enables the continuous and consistent generation of two product streams with distinct chemical composition due to the fractionation and selective incorporation of two different phospholipids in each respective product stream.

During the passage through the second and the third microchannel reactors, the injected water serves to further extract any residual water-soluble impurities such as soaps, phospholipids, residual base, and metals into a heavier aqueous phase that readily separates from the lighter oleaginous triglyceride phases as a distinct bottom layer. Water washes to remove residual ionic or water-soluble impurities can be done in one or multi-unit cascade depending on the final composition desired or targeted in the product. pH modulation in the thermodynamic microchannel reactor operation mode can serve as the tunable handle to impact the selective fractionation of specific species of phospholipids, TAGs, and DAGs and further impact spatial distribution of mass during the process.

Example 5

Crude natural cocoa butted was purified by staging a series of four microchannel fiber reactors standardized in size and pack density. In the first stage, an oleaginous mixture comprised predominantly of triglycerides, but contaminated with an initial FFA concentration of 1.84 wt %, was heated to 80° C. and pumped into the first microchannel reactor through one injection port. Through a secondary injection port on the same reactor, a 0.3 wt % aqueous solution of NaOH, also heated to 80° C., was simultaneously injected. The volumetric flow ratio of the two fluids was kept at 1:1 with an injection flowrate of 470 mL/min corresponding to a <1 minute residence time in the reactor conduit. In the separator vessel adjoined to the first reactor, the neutralized organic phase readily phased out of the aqueous effluent. As shown in FIG. 6, the concentration of FFAs in the organic stream was monitored, by titration, every hour over the course of 24 hours and averaged 0.05 wt %. This value was determined to be artificially low due to the presence of residual NaOH and the retention of 20-30% of the free fatty acid sodium salts formed but not effectively removed in the first stage. Subsequent injection of the neutralized organic stream (at 366 mL/min) comprised of 0.56 wt % soap into the second microchannel fiber reactor in which solely water is also injected at a 1:1.5 organic to aqueous volumetric flow ratio, also resulted in the facile separation of two phases in the adjoined separator vessel. The water wash in the reactor stream effectively reduced the concentration of soap in the organic triglyceride to 0.12 wt % which was sequentially reduced to 0.01 wt % after two additional microchannel reactor water wash stages. The microchannel fiber reactor neutralization/water wash cascade resulted in the production of a single distinct final refined product stream comprised of a distribution of 96.49% triglycerides, 3.24 wt % diglycerides and 0.24 wt % FFA in which >99% of the soaps formed and all screened phospholipids are efficiently removed. The results of this example are summarized in Table 2 below.

TABLE 2

| Measurement method | Measured Property | Results |
| --- | --- | --- |
| AOCS Ca 17-01 (ICP-OES) | Total Phosphorous (ppm) | 1.1 |
| AOCS Ca 6a-40 | Unsaponifiable matter (wt %) | 0.62 |
| AOCS Ca 17-01 (ICP-OES) | Iron (ppm) | <1.0 |
| HPLC | Total Diacylglycerol (wt %) | 3.24 |
| HPLC | Total Triacylglycerol (wt %) | 96.49 |
| HPLC | FFA (wt %) | 0.24 |
| AOCS Ja 7b-91 | L-α-phosphatidylethanolamine (wt %) | 0.00 |
| AOCS Ja 7b-91 | L-α-phosphatidylinositol (wt %) | 0.00 |
| AOCS Ja 7b-91 | Phosphatidylcholine (wt %) | 0.00 |
| AOCS Ja 7b-91 | L-α-lysophosphatidylcholine (wt %) | 0.00 |

Figure 8:
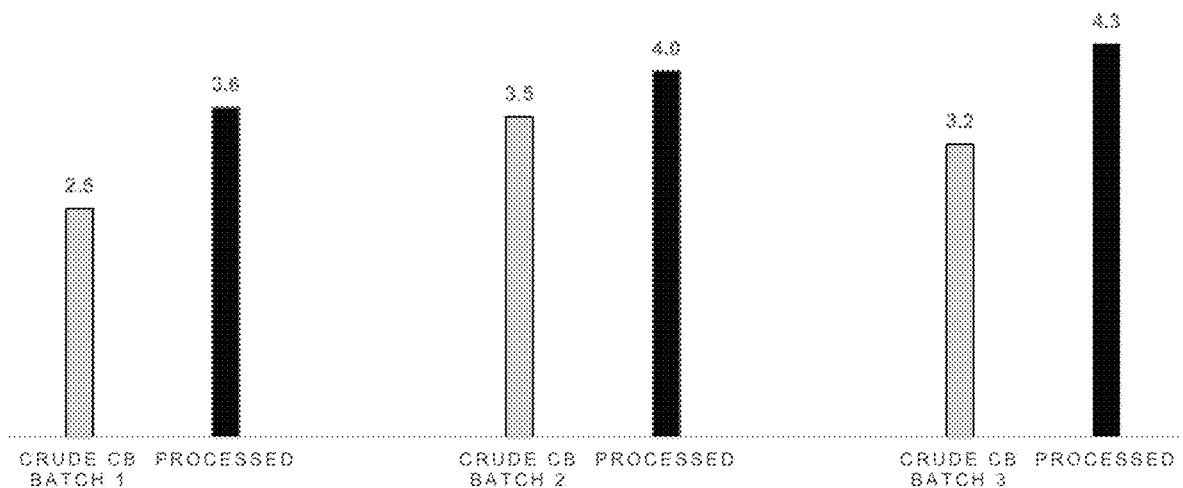
FIG. 8 is a graph showing the CBI measurements of the products of Example 5.

The sequential changes in product composition resulting from each reactor pass, as shown in FIG. 7, results in the rapid collapse and destabilization of any mechanisms that would result in intractable aggregate formation and yield losses. The outcome provides a purified product stream that is much better quality, as indicated by the increased BCI (Buhler crystallization index) values shown in two different processed examples in FIG. 8. The improved spatial distribution of lipids in cocoa butter enables rapid crystallization kinetics and the additional benefit of the sequential extractions results in significant improvement in color as indicated by changes in Lovibond values.

Example 6

In this example, operations were selected to preferentially fractionate DAGs over TAGs in the aqueous effluent using thermodynamic fractionation, as in Example 4. The composition of the matter removed from the crude natural cocoa butter was determined by the addition of acid (sulfuric acid, hydrochloric acid, phosphoric acid, and/or hydrochloric acid) to the aqueous effluent (soapstock) to re-protonate the FFA salts back into the acidic form. Upon formation, the FFAs, along with any residual lipids, readily phased out of the aqueous phase and were subsequently collected and dried. HPLC compositional analysis corroborated the presence of solely DAGs incorporated in the stream comprising of 4.37 wt % of the total mass. The results are shown below in Table 3.

TABLE 3

| Measurement method | Measured Property | Results |
| --- | --- | --- |
| AOCS Ca 6a-40 | Unsaponifiable matter (wt %) | 0.71 |
| HPLC | Total Diacylglycerol (wt %) | 4.37 |

TABLE 3-continued

| Measurement method | Measured Property | Results |
| --- | --- | --- |
| HPLC | Total Triacylglycerol (wt %) | 0 |
| HPLC | FFA (wt %) | 93.15 |
| AOCS Ja 7b-91 | L-α-phosphatidylethanolamine (wt %) | 0.00 |
| AOCS Ja 7b-91 | L-α-phosphatidylinositol (wt %) | 0.00 |
| AOCS Ja 7b-91 | Phosphatidylcholine (wt %) | 0.00 |
| AOCS Ja 7b-91 | L-α-lysophosphatidylcholine (wt %) | 1.76 |

A scalable, low-shear, multi-stage continuous process for the controlled dosing and separation of the chemicals used in the refining of high-value edible oils and butters such as natural and alkalized cocoa butter has been described herein. This disclosure describes the chemical equipment and the chemical methodology targeting the low shear interfacial contact of two immiscible streams, comprising of a crude edible oil/butter and an aqueous reactant/extractant solution, in which the aggregation behavior of the alkali treated edible oil or butter (e.g., cocoa butter) is tightly controlled within the structured microchannels packing configuration of a fiber reactor. The methods and systems described herein may improve one or more properties of an edible oil, such as reduced FFA, reduced phospholipids or ability to fractionate, reduced color, increased BCI (Buhler crystallization index), faster crystallization, and/or better lipid distribution below melting point.

Although various embodiments have been shown and described, the disclosure is not limited to such embodiments and will be understood to include all modifications and variations as would be apparent to one of ordinary skill in the art. Therefore, it should be understood that the disclosure is not intended to be limited to the particular forms disclosed; rather, the intention is to cover all modifications, equivalents, and alternatives falling within the spirit and scope of the disclosure as defined by the appended claims.

What is claimed is:
1. A method for purifying an edible oil, comprising:
simultaneously introducing the edible oil comprising at least one impurity and an aqueous reactant solution into a first end of a first microchannel fiber reactor, the first microchannel fiber reactor having a plurality of fibers disposed therein;
collecting reaction products from a reaction between the edible oil and the aqueous reactant solution in a first separator positioned proximate a second end of the first microchannel fiber reactor opposite the first end thereof, the reaction products comprising a neutralized oil and an aqueous effluent, the aqueous effluent comprising at least a portion of the at least one impurity;
separately removing the neutralized oil and the aqueous effluent from the first separator;
simultaneously introducing the neutralized oil and water into a first end of a second microchannel fiber reactor, the second microchannel fiber reactor having a plurality of fibers disposed therein;
collecting wash reaction products from a reaction between the neutralized oil and water in a second separator positioned proximate a second end of the second microchannel fiber reactor opposite the first end thereof, the wash reaction products comprising a washed oil and a second aqueous effluent, the second aqueous effluent comprising water and at least one compound from the neutralized oil;

wherein the wash reaction products further comprise a first pure edible oil and the wash reaction products form three distinct layers in the second separator.

2. The method of claim 1, wherein the edible oil is solid at room temperature and the method includes heating the edible oil to a temperature equal to or greater than a melting point of the edible oil.

3. The method of claim 1, wherein the aqueous reactant comprises an alkali solution.

4. The method of claim 1, further comprising washing the washed oil with water in a third microchannel fiber reactor to produce a second pure edible oil having a composition that is distinct from the first pure edible oil.

5. The method of claim 4, wherein the second pure edible oil has a higher content of free fatty acids than the first pure edible oil.

6. The method of claim 4, wherein the first edible oil has a different content of phospholipids as compared to the second edible oil.

7. A method for purifying an edible oil, comprising:

simultaneously introducing the edible oil comprising at least one impurity and an aqueous reactant solution into a first end of a first microchannel fiber reactor, the first microchannel fiber reactor having a plurality of fibers disposed therein;

collecting reaction products from a reaction between the edible oil and the aqueous reactant solution in a first separator positioned proximate a second end of the first microchannel fiber reactor opposite the first end thereof, the reaction products comprising a neutralized oil and an aqueous effluent, the aqueous effluent comprising at least a portion of the at least one impurity;

separately removing the neutralized oil and the aqueous effluent from the first separator;

simultaneously introducing the neutralized oil and water into a first end of a second microchannel fiber reactor, the second microchannel fiber reactor having a plurality of fibers disposed therein;

collecting wash reaction products from a reaction between the neutralized oil and water in a second separator positioned proximate a second end of the second microchannel fiber reactor opposite the first end thereof, the wash reaction products comprising a washed oil and a second aqueous effluent, the second aqueous effluent comprising water and at least one compound from the neutralized oil;

wherein a weight ratio of free fatty acids in the washed oil to free fatty acids in the edible oil is less than 0.2.

8. The method of claim 7, wherein the edible oil is solid at room temperature and the method includes heating the edible oil to a temperature equal to or greater than a melting point of the edible oil.

9. The method of claim 7, wherein the aqueous reactant comprises an alkali solution.

10. The method of claim 7, wherein the washed oil is a first pure edible oil, the wash reaction products further comprise a raffinate and the wash reaction products form three distinct layers in the second separator wherein the raffinate forms a layer between the first pure edible oil and the second aqueous effluent.

11. The method of claim 10, further comprising washing the raffinate with water in a third microchannel fiber reactor to produce a second pure edible oil having a composition that is distinct from the first pure edible oil.

12. The method of claim 10, wherein the second pure edible oil has a higher content of free fatty acids than the first pure edible oil.

13. The method of claim 10, wherein the first edible oil has a different content of phospholipids as compared to the second edible oil.

* * * * *